(12) United States Patent
Shimko et al.

(10) Patent No.: US 8,678,821 B2
(45) Date of Patent: Mar. 25, 2014

(54) DENTAL IMPLANT WITH HINGED STABLIZING ARMS

(75) Inventors: Daniel Andrew Shimko, Germantown, TN (US); Susan J. Drapeau, Cordova, TN (US); Kelly Brook Emerton, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 210 days.

(21) Appl. No.: 12/857,715

(22) Filed: Aug. 17, 2010

(65) Prior Publication Data

US 2012/0045736 A1 Feb. 23, 2012

(51) Int. Cl.
*A61C 8/00* (2006.01)

(52) U.S. Cl.
USPC ......................................... 433/173

(58) Field of Classification Search
USPC ........... 433/172–176, 201.1, 202.1, 215, 220, 433/221; 606/310, 313, 326, 327, 328; 411/30, 55, 60.1, 60.2, 60.3, 71, 80.1, 411/340, 344, 345, 32–34, 37–38; 248/217.4; 623/11.11, 16.11, 17.17, 623/17.18
IPC .............. A61C 8/00; A61B 17/66,17/70, 17/84, A61B 17/88, 17/92
See application file for complete search history.

(56) References Cited

U.S. PATENT DOCUMENTS

| | | | |
|---|---|---|---|
| 3,789,728 A * | 2/1974 | Shackelford | 411/34 |
| 3,888,156 A * | 6/1975 | Fima | 411/38 |
| 3,942,407 A | 3/1976 | Mortensen | |
| 4,022,100 A * | 5/1977 | Johnson | 411/80.5 |
| 4,269,106 A * | 5/1981 | Leibhard et al. | 411/34 |
| 4,274,324 A * | 6/1981 | Giannuzzi | 411/38 |
| 4,353,673 A * | 10/1982 | Lesowsky | 411/38 |
| 4,416,572 A * | 11/1983 | Black | 411/38 |
| 4,435,112 A * | 3/1984 | Becker | 411/368 |
| 4,531,916 A | 7/1985 | Scantlebury et al. | |
| 4,657,456 A | 4/1987 | Anquetin | |
| 4,778,320 A * | 10/1988 | Nakama | 411/509 |
| 4,828,439 A * | 5/1989 | Giannuzzi | 411/37 |
| 4,834,601 A | 5/1989 | Schaap | |
| 5,417,569 A | 5/1995 | Perisse | |
| 5,470,230 A | 11/1995 | Daftary et al. | |
| 5,509,765 A | 4/1996 | Albin | |

(Continued)

OTHER PUBLICATIONS

Flop Dental Implant, Roots, http:/www.dentalindia.com/fdid.html, pp. 1-4.

(Continued)

*Primary Examiner* — Heidi M Eide
*Assistant Examiner* — Justin O'Donnell
(74) *Attorney, Agent, or Firm* — Sorell Lenna & Schmidt LLP

(57) ABSTRACT

An implant includes a collar configured for disposal within tissue. The collar defines an axial bore. A shaft extends between a first end and a second end. The shaft is configured for disposal with the bore of the collar. A base defines an axial bore having an inner surface configured for engagement with the shaft such that the base is axially movable relative to the shaft. At least one arm extends between the collar and the base. The at least one arm is movable via axial movement of the base relative to the shaft between a first position and a second position such that the at least one arm is expanded in a configuration to engage tissue. Methods of use are also disclosed.

20 Claims, 9 Drawing Sheets

(56) References Cited

U.S. PATENT DOCUMENTS

| | | | |
|---|---|---|---|
| 5,609,635 A * | 3/1997 | Michelson | 623/17.16 |
| 5,863,200 A | 1/1999 | Hamada et al. | |
| 5,931,674 A | 8/1999 | Hanosh et al. | |
| 5,951,288 A | 9/1999 | Sawa | |
| 6,146,406 A | 11/2000 | Shluzas et al. | |
| 6,227,860 B1 | 5/2001 | Hobo | |
| 6,299,448 B1 * | 10/2001 | Zdrahala et al. | 433/173 |
| 6,511,273 B2 * | 1/2003 | Arisaka | 411/48 |
| 6,602,034 B2 * | 8/2003 | Wakai et al. | 411/37 |
| 6,755,831 B2 | 6/2004 | Putnam et al. | |
| 6,863,530 B2 | 3/2005 | McDevitt | |
| 6,991,461 B2 | 1/2006 | Gittleman | |
| 7,179,088 B2 | 2/2007 | Schulter et al. | |
| 2006/0004455 A1 * | 1/2006 | Leonard et al. | 623/17.15 |
| 2008/0213729 A1 * | 9/2008 | Hochman | 433/215 |
| 2008/0262497 A1 * | 10/2008 | Nijenbanning et al. | 606/63 |

OTHER PUBLICATIONS

Goldman, An Alternative Treatment Modality for Transitionalizing a Removable Partial Denture to a Complete Denture, http:/www.dentalaegis.com/Publications/Inside_Dentistry/article.aspx? . . . , Jun. 2006, pp. 1-2.

* cited by examiner

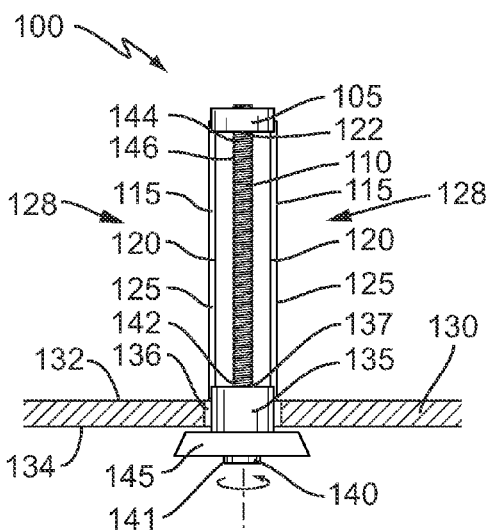
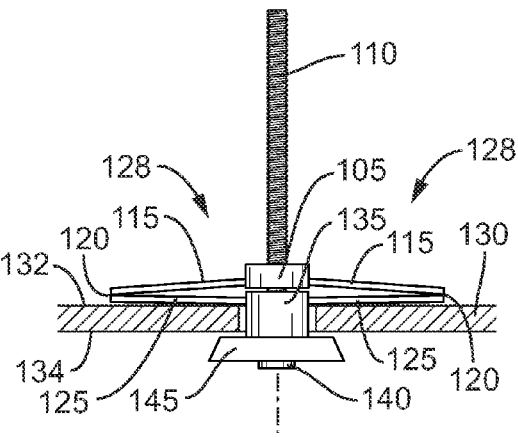
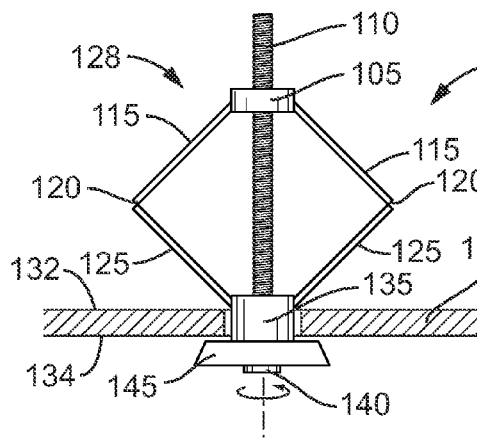
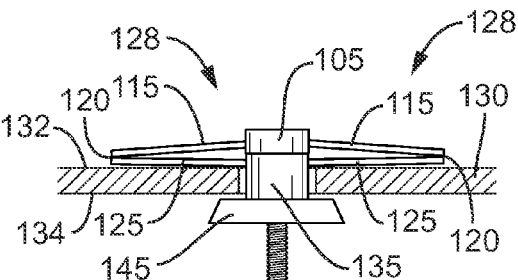
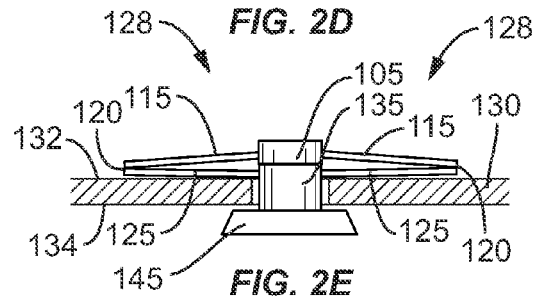

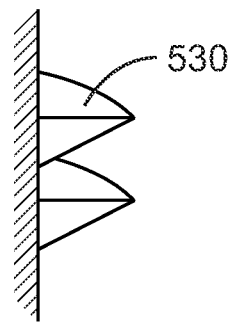
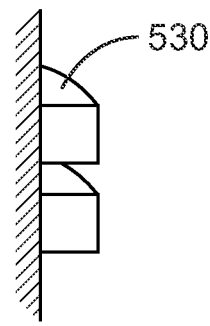
*FIG. 7A*  *FIG. 7B*
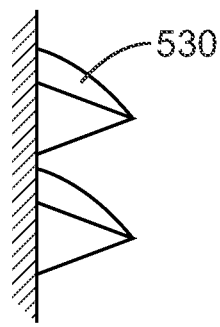
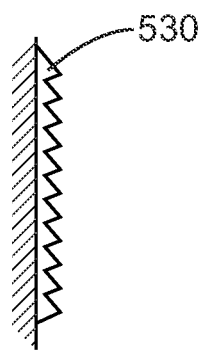
*FIG. 7C*  *FIG. 7D*
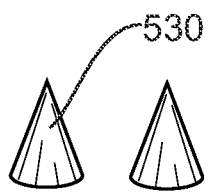
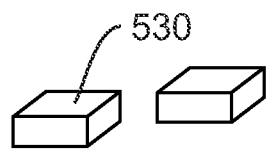
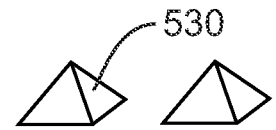
*FIG. 8A*  *FIG. 8B*  *FIG. 8C*

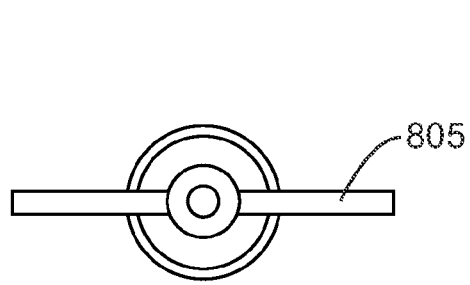
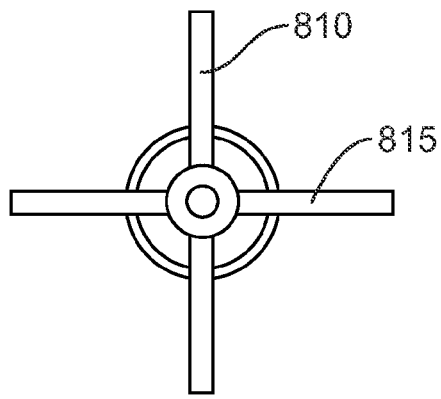
FIG. 9A  FIG. 9B
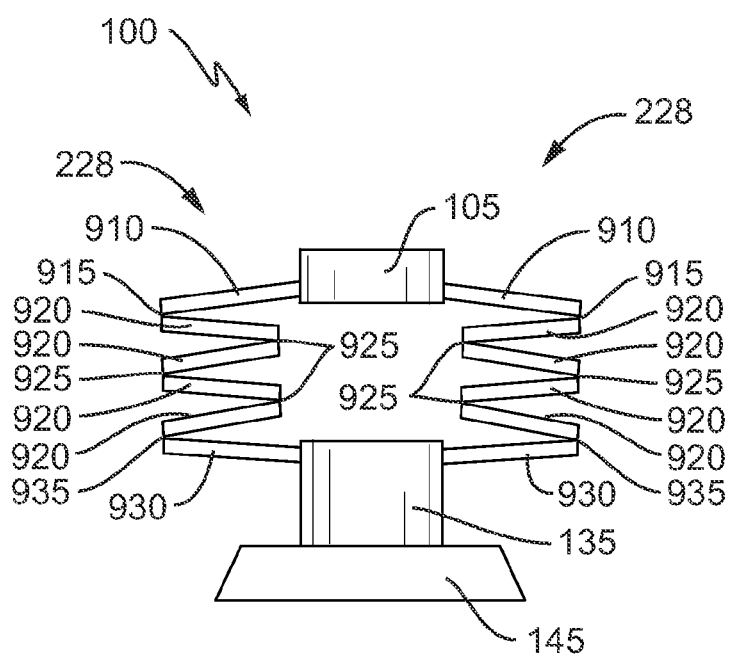
FIG. 10

DENTAL IMPLANT WITH HINGED STABLIZING ARMS

TECHNICAL FIELD

The present invention relates to implants that are surgically placed in bone to provide an anchor for a prosthesis or other device. In particular, the implant of the present invention is especially advantageous for use in dental surgery.

BACKGROUND

Implants are widely used in bone and dental surgery for restoration dentition. Implants can be used, for example, for anchoring a dental prosthesis such as an artificial tooth to the jawbone or maxilla of a patient. Various types of dental implants are disclosed, for example, in U.S. Pat. Nos. 7,179,088, 6,991,461, 6,863,530, 6,227,860, 5,951,288, 5,931,674, 5,863,200, 5,470,230, 5,417,569, and 4,531,916, all of the above references being incorporated by reference herein.

A typical dental implant has a generally cylindrical shaped body which is mounted into a hole pre-drilled into bone. Similarly, implants used to anchor to tendons/ligaments in orthopedic procedures are also mounted into pre-drilled holes in surrounding bone or in the alternative directly to tendons/ligaments. The implant can be threadedly fitted or press fitted into the hole. The prosthesis can then be fixedly mounted to the implant and secured within the bone. However, it is possible for the implant to loosen if, for example, the hole is or becomes too big, is improperly drilled, the bone has insufficient density, or the implant is placed in bone with insufficient thickness, as in a hyperpneumatized sinus. This can result in loss of the implant or prosthesis and require a subsequent operation to remedy the situation. In addition, if the implant becomes loose the resulting motion may prevent new bone growth from attaching to the implant and securing it in the bone. The present disclosure describes a dental implant that can deploy stabilizers within a formed body cavity in tissue, which may include bone, to secure a dental implant.

SUMMARY OF THE INVENTION

An implant and method of using the implant are provided herein for anchoring a prosthesis, such as an artificial tooth into bone. In one embodiment, the implant includes a collar configured for disposal within tissue. The collar defines an axial bore. A shaft extends between a first end and a second end. The shaft is configured for disposal with the bore of the collar. A base defines an axial bore having an inner surface configured for engagement with the shaft such that the base is axially movable relative to the shaft. At least one arm extends between the collar and the base. The at least one arm is movable via axial movement of the base relative to the shaft between a first position and a second position such that the at least one arm is expanded in a configuration to engage tissue.

In one embodiment, an implant system is provided in accordance with the principles of the present disclosure. The implant system includes an implant including a collar configured for disposal within tissue and defining an axial bore. The axial bore has a first diameter and a threaded inner surface. A shaft extends between a first end and a second end. The shaft is configured for disposal with the bore of the collar. A base defines an axial bore. The axial bore of the base has a second diameter less than the first diameter and an inner surface configured for threaded engagement with the shaft such that the base is axially movable relative to the shaft. At least one arm extends between the collar and the base. The at least one arm is movable via axial movement of the base relative to the shaft between a first position and a second position such that the at least one arm is expanded in a configuration to engage tissue. The shaft is removable from the implant in the expanded configuration of the at least one arm.

A sleeve is adapted to fit within the bore of the collar between the threaded inner surface of the collar and the shaft during disposal of the shaft within the axial bore of the collar. A rod extends between a first end and a second end configured to engage the base. The rod includes an outer surface configured for threaded engagement with the threaded inner surface of the collar such that the rod is axially movable relative to the collar to cause axial movement of the base such that the at least one arm is movable from the second position to the first position such that the at least one arm is disposed in substantial alignment with the rod.

In one embodiment, a dental implant is provided. The dental implant includes a collar configured for disposal within tissue having a first surface and an opposing second surface. The collar includes an axial bore defining an inner surface and a flange configured to engage the first surface of the tissue. A shaft is configured for rotation within the axial bore of the collar and defining an outer surface. A base includes an axial bore that defines an inner surface configured for threaded engagement with the other surface of the shaft such that the base is axially movable relative to the shaft. A plurality of stabilizing arms extend between the collar and the base and are disposed circumferentially about the shaft. Each arm includes a first linking member hingedly connected to a second linking member. The plurality of arms are movable via axial movement of the base relative to the shaft between a first position whereby the linking members are disposed in substantial alignment with the shaft, and a second position whereby the linking members are folded about the hinged connection such that the arms are disposed in an expanded configuration to engage the second surface of the tissue.

In one embodiment, a method for delivering an implant is provided. The method includes the step of making a hole into tissue such as a soft tissue, bone or cartilage. If the tissue is bone, then a drill can be used to bore the hole to insert the implant. For cartilage or soft tissue a scalpel can be used. The method includes the step of inserting the implant into the hole made in the tissue. Once inserted, the shaft is rotated so as to extend at least one of the outwardly extending stabilizer arms to a fully extended position thereby engaging the surrounding tissue and securing the implant in the tissue. Once the stabilizer arms are fully extended, the shaft can be rotated in the opposite direction in order to remove it from the implant. The method may further include the step of inserting a tube for providing graft material into a bore created by removing the shaft. Once inserted, graft material can be provided into said bore which can coat the implant as well as the bore. The graft material can be synthetic, natural or a mixture of the two and can include both active and non-active components.

The method can further include the step of attaching a protective biocompatible sheet configured to attach to the implant either after or before the graft material is provided into the bore.

BRIEF DESCRIPTION OF THE DRAWINGS

Various embodiments of the invention are described below with reference to the drawings, wherein:

FIG. 2A is a side view of the implant system shown in FIG. 1A in a first position engaged in tissue, shown in cross section;

FIG. 2B is a side view of the implant system engaged in tissue shown in FIG. 2A in a partially expanded configuration;

FIG. 2C is a side view of the implant system engaged in tissue shown in FIG. 2A in a second position;

FIG. 2D is a side view of the implant system engaged in tissue shown in FIG. 2C;

FIG. 2E is a side view of the implant system engaged in tissue shown in FIG. 2C with a shaft removed;

FIG. 7A is a perspective view of one particular embodiment of a protuberance of the implant system shown in FIG. 6;

FIG. 7B is a perspective view of one particular embodiment of a protuberance of the implant system shown in FIG. 6;

FIG. 7C is a perspective view of one particular embodiment of a protuberance of the implant system shown in FIG. 6;

FIG. 7D is a perspective view of one particular embodiment of a protuberance of the implant system shown in FIG. 6;

FIG. 8A is a perspective view of one particular embodiment of a protuberance of the implant system shown in FIG. 6;

FIG. 8B is a perspective view of one particular embodiment of a protuberance of the implant system shown in FIG 6;

FIG. 8C is a perspective view of one particular embodiment of a protuberance of the implant system shown in FIG. 6;

FIG. 9A is a plan view of one embodiment of the implant system shown in FIG. 2A;

FIG. 9B is a plan view of one embodiment of the implant system shown in FIG. 2A;

FIG. 10 is a side view of one embodiment of the implant system shown in FIG. 2A;

DETAILED DESCRIPTION

Figure 1A:
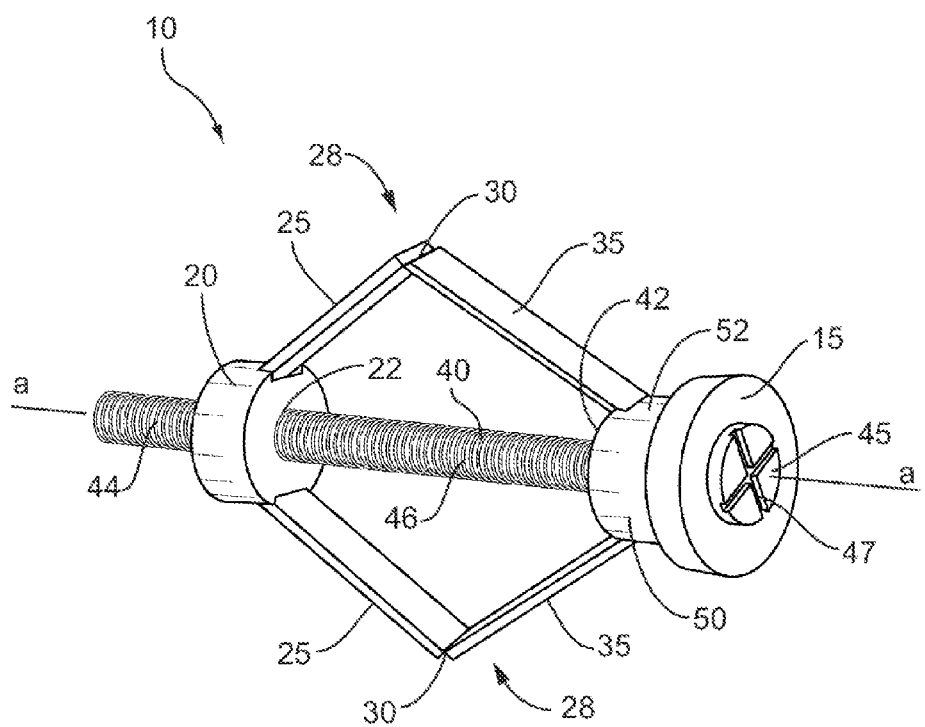
FIG. 1A is a perspective view of one particular embodiment of an implant system in accordance with the principles of the present disclosure.

The exemplary embodiments of the implant system and related methods of use disclosed are discussed in terms of medical devices for the treatment of bone disorders, such as, for example, periodontal disorders, and more particularly, in terms of a dental implant system placed in bone that employs an anchor for a prosthesis or other device to enhance treatment. It is envisioned that the dental implant system and method may include placement of permanent dental implants into an anatomy with regions of thin bone. It is further envisioned that the dental implant system includes an expandable implant that allows for placement though a hole and fixation to a thin walled bony anatomy, which allows for placement in areas of deficient bone. It is contemplated that the dental implant system and method is employed for implantation into the maxilla where a hyperpneumatized sinus may be present. It is further contemplated that the implant system may be configured as a kit.

It is envisioned that the present disclosure may be employed to treat periodontal disorders such as, for example, peri-implantitis, chronic, aggressive and necrotizing periodontitis, gingivitis and other periodontal diseases. It is contemplated that the present disclosure may be employed with other osteal and bone related applications, including those associated with diagnostics and therapeutics. The system and methods of the present disclosure may also be used on animals, bone models and other non-living substrates, such as, for example, in training, testing and demonstration.

The present invention may be understood more readily by reference to the following detailed description of the invention taken in connection with the accompanying drawing figures, which form a part of this disclosure and in which like numbers indicate like features. It is to be understood that this invention is not limited to the specific devices, methods, conditions or parameters described and/or shown herein, and that the terminology used herein is for the purpose of describing particular embodiments by way of example only and is not intended to be limiting of the claimed invention. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior". As used herein, "comprising", "containing", "characterized by" and grammatical equivalents thereof are inclusive or open-ended terms that do not exclude additional, unrecited elements or method steps, but will also be understood to include the more restrictive terms "consisting of" and "consisting essentially of".

The following discussion includes a description of an implant system, related components and exemplary methods of employing the implant system in accordance with the principles of the present disclosure. More particularly, the exemplary embodiments of the implant are particularly suitable for use in dental surgery and provide a stable anchoring for a dental prosthesis such as an artificial tooth. Additional embodiments are also disclosed. It should be noted that the implant system may also be used in any type of surgery in which a device is to be attached to bone. Accordingly, the scope of the present invention is not limited to only dental implants. Reference will now be made in detail to the exemplary embodiments of the present disclosure, which are illustrated in the accompanying figures.

The implant system, in accordance with the principles of the present disclosure, can be used to anchor prosthesis and implants in tissue. It is contemplated that tissue includes soft tissue, cartilage and/or bone. As described below and in conjunction with the figures, the components of the implant system can have different shapes and may have a biocompatible sheet or graft material deposited on an implant in the tissue.

Referring to FIG. 1A, the implant system includes an implant 10. Implant 10 includes a collar 50 that is configured for disposal within tissue (FIG. 2A) having a first surface and an opposing second surface. Collar 50 includes an axial bore defining an inner surface. It is contemplated that the bore of collar 50 may have various configurations such as, for example, circular, oval, rectangular, polygonal, angled and/or offset. It is further contemplated that collar 50 may include one or a plurality of bores. It is envisioned that the inner surface of the axial bore of collar 50 may be smooth to facilitate slidable movement of a shaft therein, non-engaging such that a shaft freely moves therein or threaded such that a shaft threadably engages the inner surface.

Collar 50 includes a flange 15 configured to engage the first surface of the tissue. Flange 15 has a larger diameter than a reduced diameter portion 52 of collar 50. This flange configuration prevents implant 10 from slipping into a cavity created for implant 10 and to hold implant 10 against the tissue in which it is inserted. It is contemplated that all or a portion of the outer surface of reduced diameter portion 52 of collar 50 and/or flange 15 may be variously configured such as, for example, smooth, arcuate, undulating and/or textured. It is further contemplated that flange 15 may have various configurations such as, for example, circular, oval, rectangular, polygonal, offset and/or staggered. It is envisioned that collar 50 may not include a flange.

Implant 10 includes a shaft 40 extending between a first end, such as, for example, a proximal end 42 and a second end, such as, for example, a distal end 44, and defines a longitudinal axis a. Shaft 40 is configured for disposal with the bore of collar 50 and defines an outer surface 46, which is threaded. Flange 15 and reduced diameter portion 52 of collar 50 have aligned inner surfaces (not shown) that define the bore of collar 50 in which shaft 40 passes through and freely rotates. It is contemplated that shaft 40 may have various cross sectional configurations such as, for example, circular, oval, rectangular, polygonal, cross and/or arcuate. It is further contemplated that all or a portion of outer surface 46 of shaft 40 may be variously configured such as, for example, smooth, arcuate, undulating and/or textured. In one embodiment, shaft 40 has a generally smooth surface that includes a releasable catch or detent that engages a base 20, discussed below, to facilitate relative axial movement.

Shaft 40 includes a head 45 defining grooves 47 that are configured to receive a tool, such as a screwdriver. Grooves 47 allow a surgeon to rotate shaft 40 so that it threads onto a base 20 as further described below. It is contemplated that the length of shaft 40 may be in a range of approximately 4 mm to 40 mm and collar 50 can have a length in a range of approximately 1 mm to 12 mm for use in dental procedures, cortical bone procedures, or other orthopedic procedures.

Figure 1B:
FIG. 1B is a perspective view of one particular embodiment of a base of the implant system shown in FIG. 1A.
Figure 1C:
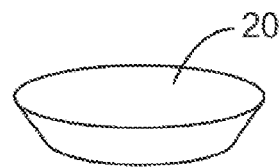
FIG. 1C is a perspective view of one particular embodiment of a base of the implant system shown in FIG. 1A.
Figure 1D:
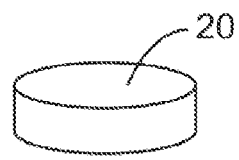
FIG. 1D is a perspective view of one particular embodiment of a base of the implant system shown in FIG. 1A.
Figure 1E:
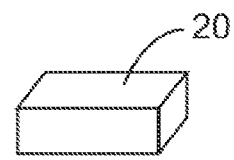
FIG. 1E is a perspective view of one particular embodiment of a base of the implant system shown in FIG. 1A.
Figure 1F:
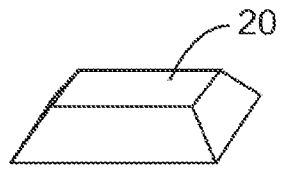
FIG. 1F is a perspective view of one particular embodiment of a base of the implant system shown in FIG. 1A.
Figure 1G:
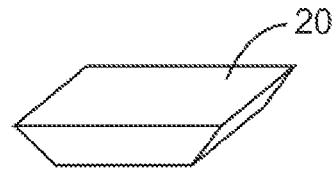
FIG. 1G is a perspective view of one particular embodiment of a base of the implant system shown in FIG. 1A.

Implant 10 includes a base 20 that defines an axial bore 22 having an inner surface that is threaded. The threaded inner surface of base 20 is configured for engagement with threaded outer surface 46 of shaft 40 such that base 20 is axially movable relative to shaft 40. Base 20 is threaded onto shaft 40 at distal end 44. Threaded bore 22 of base 20 and the bore of collar 50 are longitudinally aligned along axis a. It is contemplated that base 20 may be variously configured and dimensioned. For example, in one embodiment, as shown in FIG. 1B, base 20 tapers to a reduced diameter. In one embodiment, as shown in FIG. 1C, base 20 tapers to an increased diameter. In one embodiment, as shown in FIG. 1D, base 20 has a uniformly cylindrical configuration. In one embodiment, as shown in FIG. 1E, base 20 has a uniformly rectangular configuration. In one embodiment, as shown in FIG. 1F, base 20 has a rectangular configuration that tapers to a reduced area. In one embodiment, as shown in FIG. 1G, base 20 has a rectangular configuration that tapers to an increased area.

Implant 10 includes a plurality of stabilizing arms 28 extending between collar 50 and base 20. Arms 28 are disposed circumferentially about shaft 40. It is contemplated that implant 10 may include one or a plurality of arms 28. It is further contemplated that arms 28 may be articulating, jointed, include multiple segments that are integrally connected and/or monolithically formed. For example, in one embodiment, arms 28 can be monolithically formed in a configuration, such as, for example, bands, links, wires, cables and/or coils, which are flexible and can be bent or deformed to maintain engagement with tissue. It is envisioned that arms 28 may have various cross sectional configurations including cylindrical, polygonal, band, coiled, uniform, non-uniform and/or tapering diameter. It is further envisioned that arms 28 may be uniformly disposed about shaft 40, intersecting, mesh and/or staggered.

Each arm 28 includes a first linking member 25 hingedly connected to a second linking member 35 at a hinge 30. Initially, arms 28 are disposed in a first position (FIG. 2A, for example) whereby linking members 25, 35 are disposed in substantially parallel alignment with shaft 40. From the first position, arms 28 are movable via axial movement of base 20 relative to shaft 40 to a second position (FIG. 2D, for example) such that linking members 25, 35 are folded about hinged connection 30 such that arms 28 are disposed in an expanded configuration to engage the second surface of the tissue. It is contemplated that each arm 28 may include one or a plurality of hinge connections.

Link members 35 attach to collar 50 adjacent proximal end 42 of shaft 40. Link members 25 attach to base 20 adjacent distal end 44 of shaft 40. Arms 28 are disposed in the first position of implant 10 such that link members 25, 35 are axially aligned and arms 28 are disposed in substantially parallel alignment with shaft 40. Grooves 47 of head 45 are engaged with a tool to rotate shaft 40 in a first rotational direction, such as, for example, a clockwise direction to actuate threaded rotational engagement of shaft 40 with base 20. As shaft 40 rotates and base 20 moves axially towards collar 50, arms 28 expand to the second position, due to the threaded engagement of threaded outer surface 46 of shaft 40 with the threaded inner surface of base 20. Link members 25, 35 of each arm 28 fold at hinge 30 and extend laterally outward. Shaft 40 is rotated to bring base 20 into engagement with or adjacent to collar 50. Once fully expanded, arms 28 engage tissue to provide stabilization to the implant system such that implant 10 is maintained in place and prevented from pulling, loosening or otherwise escaping from the cavity in which it is inserted.

Upon implantation of implant 10 and disposal of arms 28 in the second position, linking members 25, 35 exert tension, such as, for example, a spring bias between hinges 30 and base 20/collar 50 to maintain arms 28 in the second position. This configuration facilitates removal of shaft 40 without causing relative axial movement of base 20 and return of arms 28 to the first position. As such, grooves 47 in head 45 are engaged with a tool to rotate shaft 40 in a second rotational direction, such as, for example, a counter-clockwise direction, which is opposite to the first rotational direction used to deploy arms 28. Counter-clockwise rotation of shaft 40 causes axial movement of shaft 40 relative to base 20 such that shaft 40 backs out of base 20 and implant 10. Shaft 40 is removed from implant 10.

Referring to FIGS. 2A-2E, in one embodiment of the implant system in assembly, operation and use, the implant system employs a dental implant 100, similar to implant 10 described above with regard to FIG. 1A, with a surgical procedure for treating periodontal disorders of a region of an anatomy of a patient. The implant system may also be employed with other surgical procedures for treatment of bone disorders such as disorders of the vertebral column.

The region of the anatomy to be treated is prepared for the surgical procedure employing the implant system of the present disclosure. The region includes tissue 130 having a first tissue surface 132 and an opposing second tissue surface 134. Tissue 130 includes gingival soft tissue and bone. Tissue 130 includes a body cavity 136 for passage and implantation of dental implant 100 therein, as shown in FIG. 2A.

Implant 100, similar to implant 10 described above with regard to FIG. 1A, includes a collar 135 configured for disposal within cavity 136. Collar 135 includes an axial bore 137. Collar 135 includes a flange 145 configured to engage surface 134 of tissue 130. This flange configuration prevents implant 100 from slipping through cavity 136 and out of fixation with tissue 130 and to hold implant 10 against tissue 130 in which it is inserted.

A shaft 110 extends between a proximal end 142 and a distal end 144. Shaft 110 is configured for disposal within bore 137 and defines a threaded outer surface 146. Shaft 110 includes a head 140 defining grooves 141 that are configured to receive a tool, such as a screwdriver. A base 105 defines an axial bore 122 having an inner surface that is threaded. The threaded inner surface of base 105 is configured for engagement with threaded outer surface 146 such that base 105 is axially movable relative to shaft 110. Base 105 is threaded onto shaft 110 at distal end 144.

Dental implant 100 includes a plurality of stabilizing arms 128 extending between collar 135 and base 105. Each arm 128 includes a first linking member 115 hingedly connected to a second linking member 125 at a hinge 120. Linking members 125 attach to collar 135 and linking members 115 attach to base 105.

Initially, arms 128 are disposed in a first position whereby linking members 115, 125 are disposed in substantially parallel alignment with shaft 110. Grooves 141 are engaged with the tool to rotate shaft 110 in a clockwise direction to actuate threaded rotational engagement of shaft 110 with base 105. From the first position, as shaft 110 rotates and base 105 moves axially towards collar 135, arms 128 expand due to the threaded engagement of threaded outer surface 146 of shaft 110 with the threaded inner surface of base 105, as shown in FIG. 2B. Linking members 115, 125 of each arm 128 fold at hinge 120 and extend laterally outward.

Arms 128 are movable via axial movement of base 105 relative to shaft 110 to a second position, as shown in FIG. 2C, such that linking members 115, 125 are folded about hinged connection 120 such that arms 128 are disposed in an expanded configuration to engage second surface 132 of tissue 130. Shaft 110 is rotated to bring base 105 into engagement with or adjacent to collar 135. Once fully expanded, arms 128 engage tissue 130 to provide stabilization to the implant system such that dental implant 100 is maintained in place and prevented from pulling, loosening or otherwise escaping from cavity 136.

Upon implantation of dental implant 100 and disposal of arms 128 in the second position, linking members 115, 125 exert tension between hinges 120 and base 105/collar 135 to maintain arms 128 in the second position. This configuration facilitates removal of shaft 110 without causing relative axial movement of base 105 and return of arms 128 to the first position. As such, grooves 141 in head 140 are engaged with the tool to rotate shaft 110 in a counter-clockwise direction, as shown in FIG. 2D. Counter-clockwise rotation of shaft 110 causes axial movement of shaft 110 relative to base 105 such that shaft 110 backs out of base 105 and dental implant 100. Shaft 110 is removed from dental implant 100, as shown in FIG. 2E. It is contemplated that an abutment and/or prosthesis may be mounted to implant 100.

Figure 3:
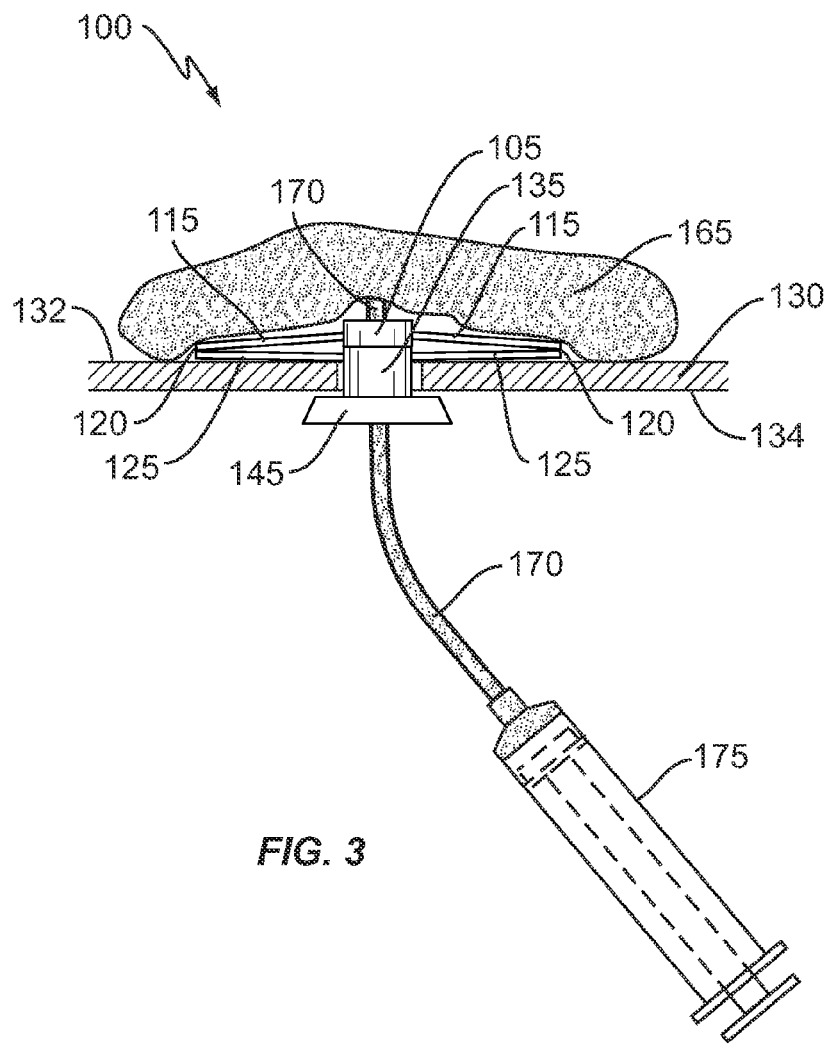
FIG. 3 is a side view of one embodiment of the implant system engaged in tissue shown in FIG. 2E with a graft applicator.

In one embodiment, as shown in FIG. 3, the implant system, similar to that discussed with regard to FIGS. 2A-2E and employing dental implant 100, includes a graft applicator 175 that is inserted within bore 137 of collar 135. Graft applicator 175 includes an applicator tube 170 that is inserted into bore 137 and the body cavity upon removal of shaft 110. Graft applicator 175 is filled with graft material 165, which is injected into the body cavity of the treated region such that graft material 165 overlays arms 128 in the second position to enhance soft tissue, cartilage and/or bone growth. It is contemplated that graft applicator 175 can have various configurations including a syringe, squeezable bag and a disposable tube.

It is envisioned that graft applicator 175 can be pre-loaded with sterile or non-sterile graft material. It is further envisioned that applicator tube 170 can be configured to fit through bore 137 and bore 122 of base 105 so that applicator tube 170 is further supported to prevent dislodging while advancing graft material 165 from graft applicator 175. Applicator tube 170 can be freely movable within bores 137, 122, or may be friction fit. Upon disposal of graft material 165 as discussed, graft applicator 175 can be removed from the treatment site.

Figure 4:
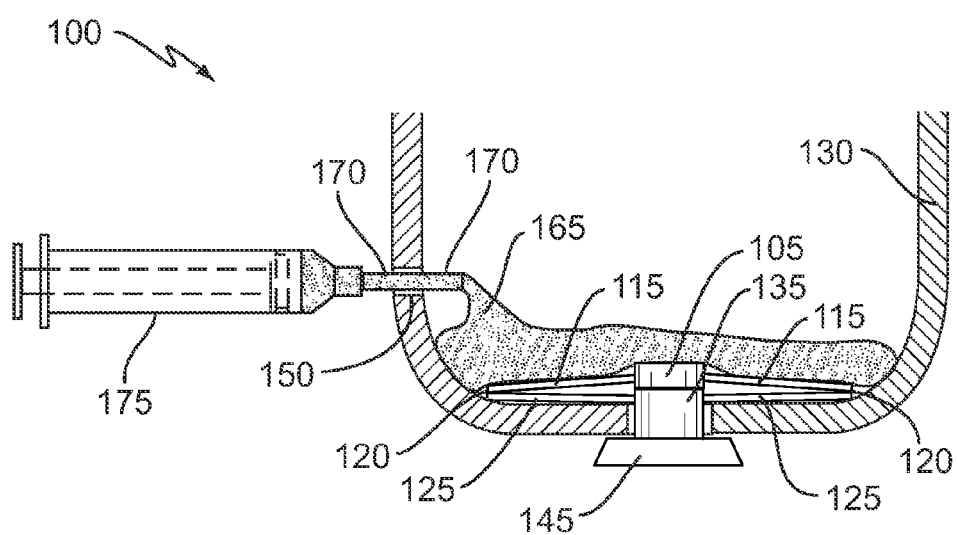
FIG. 4 is a side view of one embodiment of the implant system shown in FIG. 2E and engaged with one embodiment of tissue, shown in cross section, with a graft applicator.

In one embodiment, as shown in FIG. 4, the implant system, similar to that discussed with regard to FIG. 3 and employing dental implant 100, includes applicator tube 170 being inserted through tissue 130 by way of a lateral body cavity 150 formed in tissue 130. Graft applicator 175 is filled with graft material 165, which is injected through cavity 150 such that graft material 165 overlays arms 128 in the second position to enhance soft tissue, cartilage and/or bone growth.

It is contemplated that graft material 165 is biocompatible and can include at least one agent. The agents may include pharmacological agents, such as, for example, antibiotics, pain medications, analgesics, anesthetics, anti-inflammatory drugs including but not limited to steroids, anti-viral and anti-retroviral compounds, therapeutic proteins or peptides, therapeutic nucleic acids (as naked plasmid or a component of an integrating or non-integrating gene therapy vector system), and combinations thereof.

The agent may also include analgesics or anesthetics such as acetic acid derivatives, clonidine, COX-2 selective inhibitors, COX-2 inhibitors, enolic acid derivatives, propionic acid derivatives, salicylic acid derivatives, opioids, opioid/nonopioid combination products, adjuvant analgesics, and general and regional/local anesthetics. The agent may also include antibiotics such as, for example, amoxicillin, beta-lactamases, aminoglycosides, beta-lactam (glycopeptide), clindamycin, chloramphenicol, cephalosporins, ciprofloxacin, erythromycin, fluoroquinolones, macrolides, metronidazole, penicillins, quinolones, rapamycin, rifampin, streptomycin, sulfonamide, tetracyclines, trimethoprim, trimethoprim-sulfamthoxazole, and vancomycin.

The agent may also include immunosuppressives agents, such as, for example, steroids, cyclosporine, cyclosporine analogs, cyclophosphamide, methylprednisone, prednisone, azathioprine, FK-506, 15-deoxyspergualin, prednisolone, methotrexate, thalidomide, methoxsalen, rapamycin, leflunomide, mizoribine (Bredinin™), brequinar, deoxyspergualin, and azaspirane (SKF 105685), Orthoclone OKT™ 3 (muromonab-CD3). Sandimmune™, Neoral™, Sangdya™ (cyclosporine), Prograf™ (FK506, tacrolimus), Cellcept™ (mycophenolate motefil, of which the active metabolite is mycophenolic acid), Imuran™ (azathioprine), glucocorticosteroids, adrenocortical steroids such as Deltasone™ (prednisone) and Hydeltrasol™ (prednisolone), Folex™ and Mexate™ (methotrxate), Oxsoralen-Ultra™ (methoxsalen), Rapamuen™ (sirolimus), BMP-2, BMP-7, GDF-5, DBM, PDGF, and Amelogenins.

The agents may also include adhesives, cement, bone fillers, autografts, ceramics, InFuse® or other bone growth stimulating proteins, DBMs, and the like. Graft material 165 can facilitate bone growth above implant 100 and over arms 128 to secure implant 100 and strengthen tissue surrounding implant 100. For example, implant 100 can be used to place a tooth while strengthening bone.

Figure 5A:
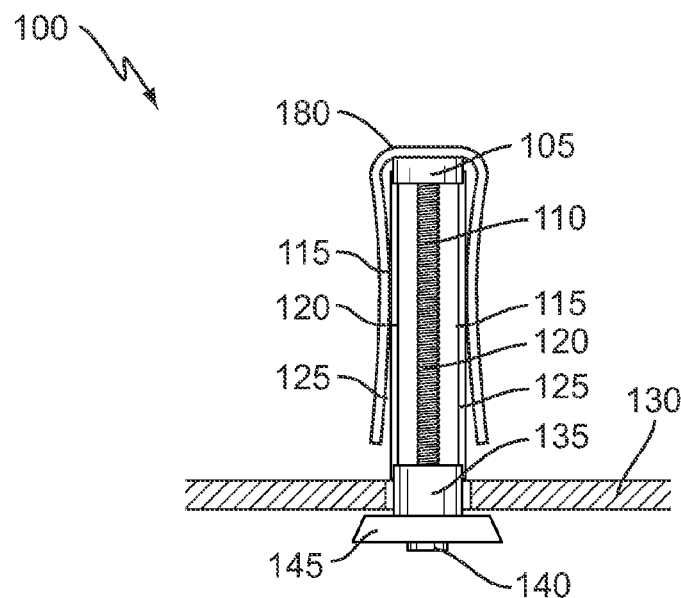
FIG. 5A is a side view of one embodiment of the implant system shown in FIG. 2A with a biocompatible sheet.
Figure 5B:
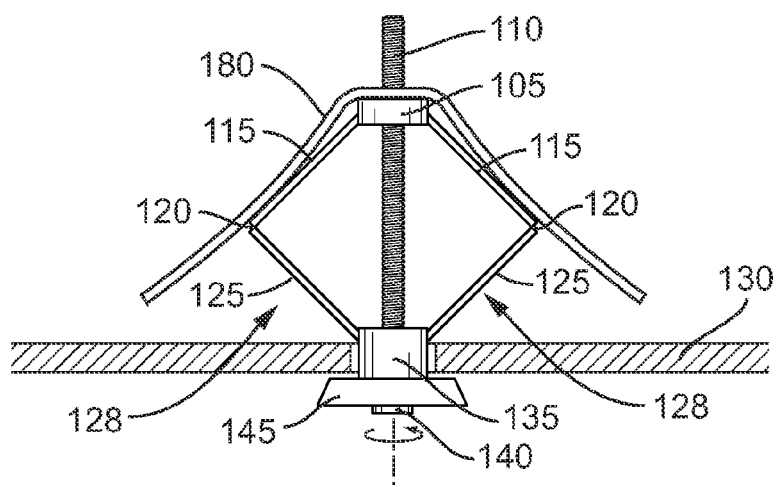
FIG. 5B is a side view of the implant system shown in FIG. 5A in a partially expanded configuration.
Figure 5C:
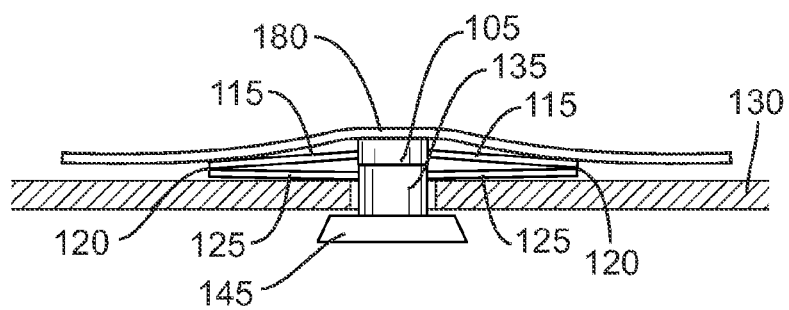
FIG. 5C is a side view of the implant system shown in FIG. 5A in a second position.

In one embodiment, as shown in FIGS. 5A-5C, the implant system, similar to that discussed with regard to FIGS. 2A-2E and employing dental implant 100, includes a biocompatible layer, such as, for example, a biocompatible sheet 180 configured to overlay base 105 and/or stabilizer arms 128. In the first position, discussed above, biocompatible sheet 180 overlies and is attached to base 105 and drapes or covers arms 128 in the unexpanded configuration, as shown in FIG. 5A.

As shaft 110 rotates and base 105 moves axially towards collar 135, arms 128 expand, as shown in FIG. 5B. Linking members 115, 125 of each arm 128 fold at hinge 120 and extend laterally outward such that biocompatible sheet 180 expands to overlie arms 128.

In the second position, as shown in FIG. 5C, arms 128 are fully expanded with biocompatible sheet 180 such that biocompatible sheet 180 has a flattened or substantially even configuration to overlay arms 128. It is contemplated that biocompatible sheet 180 may be flexible or semi-flexible, or include adhesive for attachment with the surfaces of dental implant 100. Additional adhesive can be applied to either the surrounding tissue or the under surface of the biocompatible sheet 180. It is envisioned that biocompatible sheet 180 may reduce friction, protect the components of the implant system, and be impregnated or deposited with agents such as those described herein.

Figure 6:
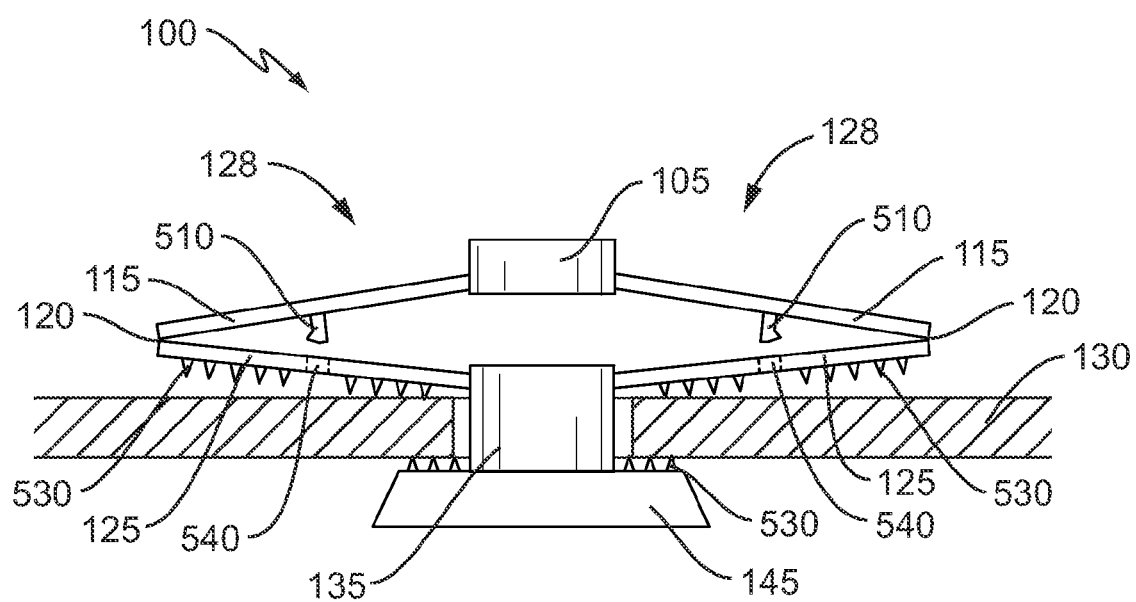
FIG. 6 is a side view of one embodiment of the implant system shown in FIG. 2A in a second position.

In one embodiment, as shown in FIG. 6, the implant system, similar to that discussed with regard to FIGS. 2A-2E and employing dental implant 100, includes linking member 115 including a locking element 510 and linking member 125 defining an opening, such as, for example, a locking port 540 configured for disposal of locking element 510. In the second position, locking element 510 is fixed within locking port 540 to lock arms 128 in the second position. As base 105 moves axially to engagement with or adjacent to collar 135, locking element 510 passes through locking port 140 to resiliently engage linking member 125 and come to rest for locking linking members 115, 125. It is envisioned that locking element 510 may be releasably lockable with locking port 140. It is further envisioned that the locking element may include clips, pins and/or spring loaded elements, which can be manually or mechanically actuated. One or more of arms 128 may include locking elements/ports. In the second position of implant 100, shaft 110 can be detached from implant 100.

Linking members 125 and/or flange 145 may include tissue gripping elements, such as, for example, a plurality of protuberances 530 projecting therefrom. Protuberances 530 are configured to engage and/or penetrate tissue 130 to facilitate engagement and fixation of the components of dental implant 100 with tissue 130 by either partially embedding into tissue 130 and/or creating friction between the components of dental implant 100 and tissue 130 to further secure the implant. It is contemplated that protuberances 530 may be variously configured and dimensioned. For example, in one embodiment, as shown in FIG. 7A, protuberances 530 have an axial spike configuration. In one embodiment, as shown in FIG. 7B, protuberances 530 gradually increase in area to a rectangular configuration. In one embodiment, as shown in FIG. 7C, protuberances 530 have an angled spike configuration. In one embodiment, as shown in FIG. 7D, protuberances 530 have a serrated configuration. In one embodiment, as shown in FIG. 8A, protuberances 530 have a conical configuration. In one embodiment, as shown in FIG. 8B, protuberances 530 have a rectangular configuration. In one embodiment, as shown in FIG. 8C, protuberances 530 have a pyramid configuration.

In one embodiment, as shown in FIG. 9A, the implant system, similar to that discussed with regard to FIGS. 2A-2E and employing dental implant 100, includes head 140 of shaft 110 having levers 805 that are manipulable to cause rotation of shaft 110, as discussed above. Levers 805 are rotated about longitudinal axis a to effect rotation of shaft 110. In one embodiment, as shown in FIG. 9B, head 140 includes diametrically opposing arms 810 and 815, which are manipulable to cause rotation of shaft 110.

In one embodiment, as shown in FIG. 10, the implant system, similar to that discussed with regard to FIGS. 2A-2E and employing dental implant 100, includes arms 228, similar to arms 128 discussed above, having a plurality of linking members and a plurality of hinge connections. Arms 228 include a first linking member 910 connected to a plurality of intermediate linking members 920 at a hinge 915. Linking members 920 are interconnected by hinges 925. Linking members 920 are connected to a second linking member 930 at a hinge 935, which is connected to collar 135. First linking member 910 is connected to base 105.

The multiple linking member and hinge configuration of arms 228 decreases the distance that arms 228 outwardly extend without a loss in holding strength. The number of stabilizer arms 228 is inversely proportional to the distance which arms 228 extend in the expanded configuration. It is envisioned that arms 228 can be employed in constricted or restricted treatment regions and/or in conditions where dental implant 100 is subjected to high levels or duration of force/pressure.

It is further envisioned that arms 228 can be employed when the thickness or density of tissue 130 has an undesirably small thickness or density for implantation. Arms 228 distribute forces exerted thereon and delocalize direct forces exerted on implant 100 to reduce the possibility of the implant becoming dislodged and/or damaging tissue 130.

Figure 11:
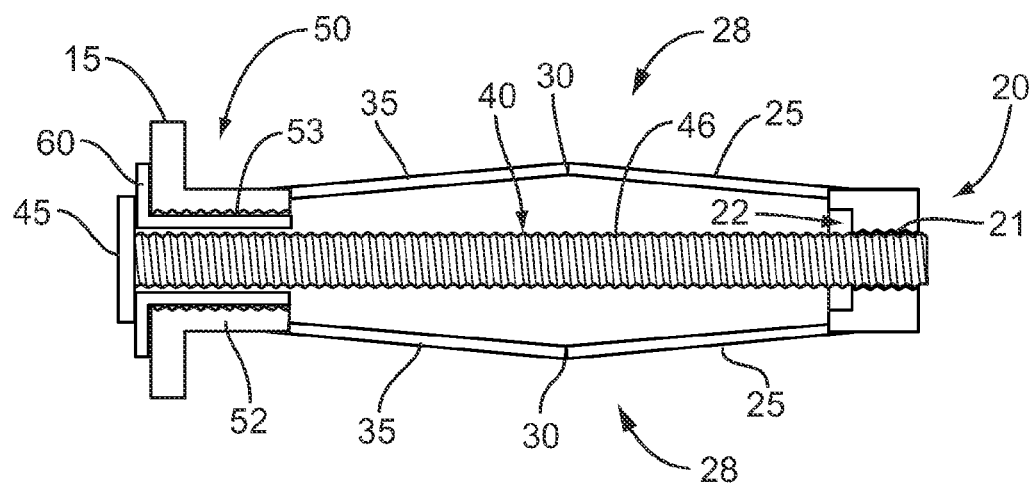
FIG. 11 is a side view of one embodiment of the implant system shown in FIG. 1A.
Figure 12:
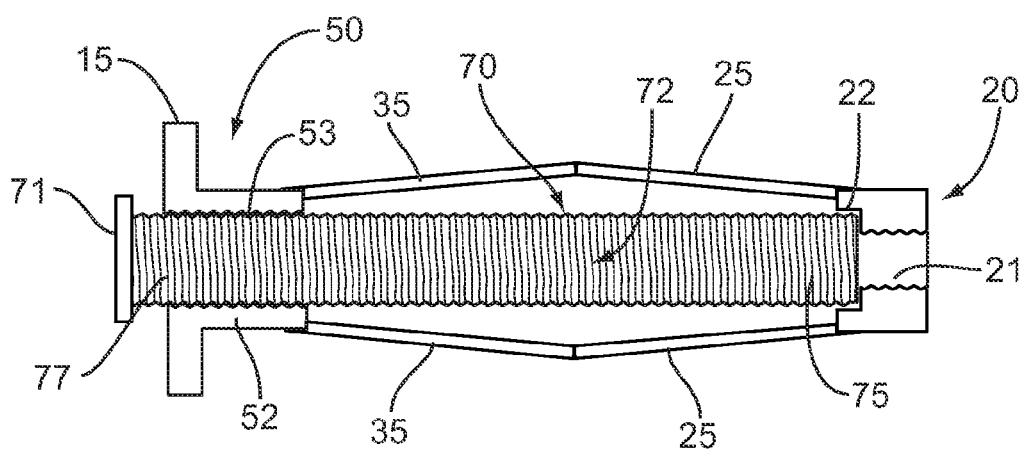
FIG. 12 is a side view of the implant system shown in FIG. 11 with a removal shaft.
Figure 13:
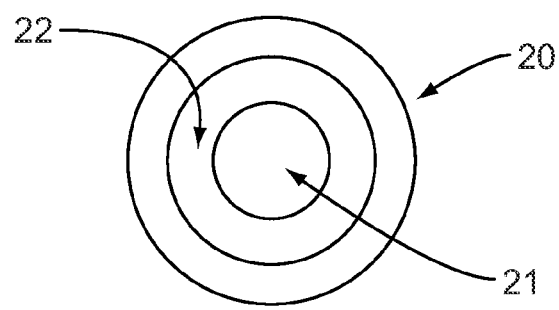
FIG. 13 is a plan view of the implant system shown in FIG. 11.

In one embodiment, as shown in FIGS. 11-13, the implant system, similar to that discussed with regard to FIG. 1A and employing dental implant 10, is configured as a kit whereby implant 10 is removable subsequent to implantation with tissue. The implant system includes a sleeve 60 configured for disposal within an axial bore 53 of collar 50. Axial bore 53 defines a threaded inner surface. Sleeve 60 is adapted to fit between the threaded inner surface of collar 50 and shaft 40 during disposal of shaft 40 within axial bore 53. Sleeve 60 is disposed through bore 53 to prevent engagement of the threaded inner surface of bore 53. It is contemplated that sleeve 60 can be fabricated from any suitable material such as ceramic, metal, plastic (e.g., polyvinyl chloride, polytetrafluoroethylene, polyethylene, and the like). Threaded bore 53 has a larger diameter than a threaded bore 21 in base 20.

As shaft 40 is rotated to cause relative axial movement of base 20, as discussed above, threaded outer surface 46 of shaft 40 freely rotates and does not interfere with the threaded inner surface of bore 53 due to the spacing of sleeve 60. The diameter of shaft 40 is less than the diameter of threaded bore 53 and as such, shaft 40 freely rotates without threaded engagement. As arms 28 are disposed in the second position and implant is fixed into engagement with tissue, shaft 40 is removed from implant 10, as discussed above. Sleeve 60 is slidably removed.

Implant 10 is removable. It is contemplated that removal of implant 10 may be desired for various conditions including improper implantation, infection, rejection and/or implant position adjustment. For removal of implant 10 from the tissue subsequent to implantation, the implant system includes a rod 70. Rod 70 extends between a first end 75 and a second end 77 configured to engage a cylindrical recess 22 of base 20. Rod 70 includes a threaded outer surface 72 configured for threaded engagement with the threaded inner surface of bore 53 such that rod 70 is axially movable relative to collar 50.

Rod 70 has a head 71 disposed adjacent first end 77 adapted for engagement with a tool for rotating rod 70, similar to head 45. The diameter of rod 70 corresponds to the diameter of bore 53 for threaded engagement, however, is larger than threaded bore 21 to prevent threaded engagement with base 20. Axial movement of rod 70 causes second end 75 to engage recess 22 and axially move base 20 from the second position to the first position of arms 28.

Arms 28 collapse such that linking members 25, 35 are disposed in substantially parallel alignment with rod 70. As such, implant 10 can be manipulated and removed from the tissue.

The components of the implant system may be fabricated from materials suitable for medical applications, including metals, synthetic polymers, ceramics, bone, biocompatible materials and/or their composites, depending on the particular application and/or preference of a medical practitioner. For example, components of the implant system can be fabricated from materials such as commercially pure titanium, titanium alloys, Grade 5 titanium, super-elastic titanium alloys, cobalt-chrome alloys, stainless steel alloys, superelastic metallic alloys (e.g. Nitinol, super elasto-plastic metals, such as GUM METAL® manufactured by Toyota Material Incorporated of Japan), thermoplastics such as polyaryletherketone (PAEK) including polyetheretherketone (PEEK), polyetherketoneketone (PEKK) and polyetherketone (PEK), carbon fiber reinforced PEEK composites, PEEK-BaSO$_4$ composites, ceramics and composites thereof such as silicon substituted calcium phosphate (e.g. SKELITE™), rigid polymers including polyphenylene, polyamide, polyimide, polyetherimide, polyethylene, polyurethanes of any durometer, epoxy and/or silicone. Different components of the implant system may have alternative material composites to achieve various desired characteristics such as strength, rigidity, elasticity, compliance, biomechanical performance, durability and radiolucency or imaging preference. The components of the implant system may also be fabricated from a heterogeneous material such as a combination of two or more of the above-described materials.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An implant comprising:
a collar configured for disposal within tissue, the collar defining a threaded axial bore;
a shaft including a threaded outer surface and extending between a first end and a second end, the first end of the shaft being disposed with the axial bore of the collar such that the threads on the outer surface of the shaft engage the threaded axial bore;
a base defining an axial bore including a threaded inner surface, the second end of the shaft being disposed within the axial bore of the base such that the threads on the outer surface of the shaft engage the threaded inner surface of the base and the base is axially movable relative to the collar; and
at least one arm extending between the collar and the base including a first linking member engaged with the base, the first linking member having a hinged connection to a second linking member engaged with the collar, the first linking member including a locking element projecting from a surface of the first linking member and the second linking member defining an opening configured for disposal of the locking element, the at least one arm being movable via axial movement of the base relative to the shaft between a first position in which the collar and the base are separated by a first distance and the first linking member is spaced apart from the second linking member, and a second position in which the collar and the base are separated by a second, reduced distance and the first linking member engages the second linking member such that the locking element is fixed within the opening to lock the at least one arm in the second position.

2. The implant of claim 1, wherein said inner surface is configured for threaded engagement with an outer surface of the shaft such that the base is axially movable relative to the shaft.

3. The implant of claim 1, wherein said at least one arm includes a plurality of stabilizing arms disposed circumferentially about the shaft.

4. The implant of claim 1, wherein said at least one arm includes at least one tissue gripping element projecting therefrom.

5. The implant of claim 1, wherein the at least one arm includes the first and second hingedly connected linking members such that in the first position the first and second hingedly connected linking members are disposed in parallel with the shaft and in the second position the first and second hingedly connected linking members are folded about the hinged connection.

6. The implant of claim 1, wherein said shaft is rotatable to actuate axial movement of the base relative thereto such that the shaft freely rotates within the axial bore of the collar.

7. The implant of claim 1, further comprising a protective biocompatible layer configured to overlay said at least one arm in the second position.

8. The implant of claim 7, wherein said protective biocompatible layer includes at least one agent.

9. The implant of claim 1, wherein the base extends between a first surface and an opposite second surface, the first surface facing the collar, the second end of the shaft including a first face extending transverse to a longitudinal axis defined by the shaft, the first face extending through the second surface when the at least one arm is in the first and second positions, the first face being positioned a first distance from the second surface when the at least one arm is in the first position, the first face being positioned a second, greater distance from the second surface when the at least one arm is in the second position.

10. The implant of claim 1, wherein the at least one arm moves from the first to the second position by rotating the shaft.

11. An implant system comprising:
an implant including:
a collar configured for disposal within tissue and defining an axial bore, the axial bore of the collar having a first diameter and a threaded inner surface,
a shaft extending between a first end and a second end, the first end of the shaft being disposed within the bore of the collar,
a base defining an axial bore, the axial bore of the base having a second diameter less than the first diameter and an inner surface threadingly engaging the second end of the shaft such that the base is axially movable relative to the collar,
at least one arm extending between the collar and the base including a first linking member having a hinged connection to a second linking member, the first linking member including a locking element and the second linking member defining an opening configured for disposal of the locking element, the at least one arm being movable from a first position in which the collar and the base are separated by a first distance and the first linking member is spaced apart from the second linking member, to a second position in which the collar and the base are separated by a second, reduced distance and the first linking member engages the second linking member such that the locking element is fixed within the opening to lock the at least one arm in the second position, and
a sleeve adapted to fit within the bore of the collar between the threaded inner surface of the collar and the shaft during disposal of the shaft within the axial bore of the collar;
wherein the at least one arm moves from the first to the second position by rotating the shaft.

12. The implant system of claim 11, further comprising an applicator configured to overlay graft material onto the implant.

13. The implant system of claim 12, wherein the applicator includes a tube configured to be disposed within the bore of the collar upon removal of the shaft.

14. The implant system of claim 11, further comprising a protective biocompatible sheet configured to overlay the at least one arm.

15. The implant system of claim 11, wherein said at least one arm includes a plurality of stabilizing arms disposed circumferentially about the shaft.

16. The implant system of claim 11, wherein said at least one arm includes at least one tissue gripping element projecting therefrom.

17. The implant system of claim 11, wherein the at least one arm includes the first and second hingedly connected linking members such that in the first position the first and second hingedly connected linking members are disposed in substantial alignment with the shaft, and in the second position the first and second hingedly connected linking members are folded about the hinged connection.

18. A dental implant comprising:
a collar configured for disposal within tissue having a first surface and an opposing second surface, the collar including an axial bore defining a threaded inner surface and a flange configured to engage the first surface of the tissue;
a shaft including a threaded first end rotatably disposed within the axial bore of the collar such that the threaded first end engages the threaded inner surface, the shaft defining an outer surface;
a base including an axial bore defining a threaded inner surface, a threaded second end of the shaft engaging the axial bore of the base such that the threaded second end engages the threaded inner surface of the base and the base is axially movable relative to the collar;
a plurality of stabilizing arms extending between the collar and the base and being disposed circumferentially about the shaft, each of the plurality of stabilizing arms including a first linking member having a hinged connection to a second linking member, wherein the first linking member includes a locking element and the second linking member defines an opening configured for disposal of the locking element such that in a second position the locking element is fixed within the opening to lock the stabilizing arms in the second position, and
wherein the plurality of stabilizing arms are movable via axial movement of the base relative to the shaft between a first position whereby the first and second linking members are disposed in substantial alignment with the shaft, and the second position whereby the first and second linking members are folded about the hinged connection such that the plurality of stabilizing arms are disposed in an expanded configuration to engage the second surface of the tissue.

19. The dental implant of claim 18, wherein said plurality of stabilizing arms include tissue gripping elements projecting therefrom.

20. The dental implant of claim 18, wherein the collar and the base are separated by a first distance and the first linking member is spaced apart from the second linking member when the plurality of stabilizing arms are in the first position, and the collar and the base are separated by a second, reduced distance and the first linking member and the second linking member of each of the plurality of stabilizing arms are engaged when the plurality of stabilizing arms are in the second position.

* * * * *